United States Patent [19]

Pearce

[11] Patent Number: 4,971,065

[45] Date of Patent: Nov. 20, 1990

[54] TRANSDUCER FOR DETECTING APNEA

[76] Inventor: Stephen D. Pearce, 14 Malabu Dr., Highland Heights, Ky. 41076

[21] Appl. No.: 700,557

[22] Filed: Feb. 11, 1985

[51] Int. Cl.⁵ .................... A61B 5/08; A61B 5/113; G01L 1/22
[52] U.S. Cl. .................................. 128/721; 128/782; 338/2
[58] Field of Search ............ 128/716, 721, 722, 782; 73/774; 338/2, 5, 114

[56] References Cited

U.S. PATENT DOCUMENTS

| | | | |
|---|---|---|---|
| 2,445,660 | 7/1948 | Bruestle | 338/114 |
| 2,734,978 | 2/1956 | Bulgin | 338/114 |
| 3,184,962 | 5/1965 | Gay | 73/774 X |
| 3,836,900 | 9/1974 | Mansfield | 128/721 |
| 3,926,177 | 12/1975 | Hardway et al. | 128/722 |
| 4,294,015 | 10/1981 | Drouin et al. | 128/782 X |
| 4,444,205 | 4/1984 | Jackson | 128/782 |
| 4,474,185 | 10/1984 | Diamond | 128/722 |

FOREIGN PATENT DOCUMENTS 1557588 12/1979 United Kingdom ............... 338/114

*Primary Examiner*—Kyle L. Howell
*Assistant Examiner*—John C. Hanley
*Attorney, Agent, or Firm*—Frost and Jacobs

[57] ABSTRACT

A transducer element particularly adapted for use in an apnea detection system is formed of resilient conductive material having an electrical impedance which varies in response to breathing movement of an infant. A control detects the varying impedance and generates an alarm signal whenever variations caused by breathing movements fall below a predetermined level.

1 Claim, 2 Drawing Sheets

==END==

TRANSDUCER FOR DETECTING APNEA

TECHNICAL FIELD

This invention relates generally to transducer element monitoring devices and more particularly concerns a transducer element for modifying an electrical signal in response to movements of a subject mechanically interfaced with the transducer element. The invention will be specifically disclosed in connection with an apnea detection system for monitoring an electrical output signal from a transducer element and activating an alarm when movement of a subject mechanically interfaced with the transducer element ceases for a predetermined time period.

BACKGROUND OF THE INVENTION

Sleep apnea, the cessation of breathing due to unknown causes, continues to tragically affect the lives of families with infants. Clinical data suggests that the incidence of infant mortality attributable to breathing cessation from unknown causes, also know as sudden infant death syndrome or crib death, is approximately one per 500 apparently normal infants.

For some time it has been recognized that an infant experiencing sleep apnea can be saved if the condition is immediately detected, and steps toward resuscitation are promptly taken. The prior art is replete with monitoring/alarm devices intended to accomplish this goal by detecting the cessation of breathing and subsequently sounding an alarm.

Of the various types of monitoring devices disclosed in the prior art, the only type which has achieved any appreciable commercial success utilizes electrodes which are physically attached to the infant's chest. These attached electrode type devices are capable of monitoring even the most subdued breathing motions of an infant. Unfortunately, the high cost of these monitors precludes their use in the average home. This same high cost also practically limits the use of these monitors in hospitals to those infants considered to be at high risk. Even when home monitoring is prescribed for a high risk infant, the substantial rental fees that are charged for these attached electrode type monitoring devices often discourage monitoring for the full 18 month period during which infants are generally considered to be susceptible to crib death.

In addition, all attachable monitoring devices, including the attached electrode type devices described above, have inherent shortcomings. Each time the infant is put down to (or picked up from) sleep, the sensing means must be connected to (or disconnected from) the infant. For example, in the previously described attached electrode types, the electrodes must be taped or otherwise secured to the infant's body. In addition to the inconvenience of attaching and detaching these devices, attached monitoring devices often cause discomfort for the infant. Moreover, attached devices are readily tampered with by older children or by the infant himself; or the devices may become unattached during normal sleeping movement of an infant. Detachment of such attachment monitoring devices, of course, renders them inoperative.

In order to overcome the inherent shortcomings of the attached type monitoring devices described above, numerous prior art attempts have been made to develop nonattached devices for detecting the cessation of infant breathing. These nonattached devices typically include an electromechanical transducer element which modifies an electrical signal in response to detected mechanical movement. For example, in U.S. Pat. No. 3,991,746 to Hanna and U.S. Pat. No. 3,926,177 to Hardway et al, first and second flexible conductive sheets separated by an electrically insulating sheet are placed beneath a subject. When a carrier frequency is applied to the conductive sheets, movement of the subject varies the capacitance between the conductive sheets. This variation in capacitance is detected to provide an indication of the subject's movement. Other monitoring systems, such as disclosed in U.S. Pat. No. 3,727,606 to Sielaff have used fluid filled mattresses and have detected variations in fluid pressure produced by movement of the subject to provide an indication of breathing.

Virtually all of the prior art monitoring devices are capable of detecting gross movement. However, in order to be effective in detecting apnea in infants, a device must be able to reliably detect and monitor relatively minor movements which result from infant breathing. This task is compounded when the transducer element area is expanded to cover any reasonable size sleeping area, even, for example, an expansion adequate to cover an infant's crib. Typically, increasing the size of the detection area lowers the overall transducer element sensitivity. Moreover, sheets, mattress covers and clothing worn by an infant all tend to mask the infant's breathing movement, making detection of such movement more difficult.

Unfortunately, simply increasing the gain of the signal conditioning electronics used in connection with prior art nonattached monitoring transducers does not provide a satisfactory solution. Electrical background noise is amplified by the same amount as movement induced signals, and such amplified background noise may be falsely interpreted by the electronics as movement of an infant. Failure to distinguish electrical background noise from movement may falsely indicate that the infant is moving when no such movement has occurred, and may preclude activation of an alarm. This, of course, can be fatal to an infant experiencing apnea. On the other hand, reducing the gain to avoid detection of electrical background noise reduces the ability of the system to detect subdued breathing movements of an infant and results in false alarms. Such false alarms, often occurring in the middle of the night, further disrupt the lives of already worried parents.

One prior art device which attempts to overcome the problem of transducer element insensitivity resulting from enlarging the detection area to cover a reasonable size sleeping area is disclosed in U.S. Pat. No. 3,836,900 to Mansfield. Mansfield discloses a device which utilizes a number of layers of resilient resistor material arranged so that movement of one layer relative to a contiguous layer changes the contact resistance between layers. The sensor material in Mansfield is arranged in a parallel fashion to cover a normal size sleeping area. While that manner of paralleling the sensor material dampens the response of the transducer element, it has a much more significant and positive effect of increasing the signal amplitude being monitored. However, this method of enhancing the signal presents new problems associated with the edge effects of the sensor material. In other words, the relative movement between the layers of sensor material generates variable and unpredictable contact resistance. This causes undesirable spurious signals, which may be misinterpreted by the electronics as movement of a subject being monitored. As a consequence, the signal conditioning circuitry of Mansfield must include a means for reducing the amplification of the transducer element signal in order to suppress or attenuate those edge effects which result from the resilient material slowly returning to its predisturbed state. Such an attenuation control would have to be properly adjusted by the user according to the size and weight of the infant being monitored, because the magnitude of the edge effects is directly dependent upon these two factors. Too much attenuation results in false signals, and too little attenuation may prevent an apnea condition from being detected.

SUMMARY OF THE INVENTION

Accordingly, it is a primary object of the present invention to provide a low cost nonattached transducer element for detecting movement of a subject mechanically interfaced with the transducer element.

It is another object of the present invention to provide a transducer element which is capable of reliably monitoring subdued breathing movements of infants over a reasonable size detection area.

A further object of the invention is to provide a highly sensitive movement detection system that is capable of distinguishing between electrical background noise and small movements of a subject mechanically interfaced with a transducer element.

Another object of the present invention is to provide a highly sensitive transducer element with a detection area that may be expanded to cover a normal size sleeping area.

Yet another object of the invention is to provide a highly sensitive movement detecting transducer element system that minimizes the detection of electrical background noise which may be misinterpreted as movement by the control circuitry.

Still another object of the invention is to provide a low cost, reliable, nonattached apnea detection system that may routinely be used for monitoring even low risk infants against apnea.

Additional objects, advantages and other novel features of the invention will be set forth in part in the description that follows and in part will become apparent to those skilled in the art upon examination of the following, or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention described herein, a novel transducer element is provided for monitoring movement of a subject mechanically interfaced with the transducer element. The transducer element includes a continuous electrically conductive path formed of resilient electrically resistive material. The conductive path has a width which is relatively narrow with respect to its length and has an electrical resistance which varies in response to variable deformations of localized areas of the resilient material. The conductive path is configured into a serpentine shape to form a series of legs joined by turns for covering a predetermined detection area. Means are provided for electrically insulating the serpentine legs from each other except through the conductive path turns. An electrical conductor is connected to each end of the serpentine path, the conductors being electrically connected in series with each other through the conductive path.

In a preferred form of the invention, the opposite longitudinal ends of the continuous conductive path are positioned in juxtapositional relationship to each other.

In another aspect of the invention, the conductive path is formed of a plastic foam.

In one preferred form of the invention, the foam has conductive values in the semiconductive range.

In another preferred form of the invention, the foam is impregnated with graphite.

In a further aspect of the invention, the electrical insulating means includes a substrate. The foam path is secured to the substrate to maintain a spacing between adjacent legs of the serpentine path.

In another aspect of the invention, the electrical insulating means includes an air space between adjacent legs of the serpentine path.

According to another aspect of the invention, wire attachment means are provided for electrically interfacing the conductive path to wires at opposite longitudinal ends of the path.

In a further aspect of the invention, a flexible nonconductive means is provided for enclosing the continuous conductive path.

Preferably, the enclosure means is waterproof.

According to yet another object of the invention, the substrate is formed of nonconductive foam material.

In yet another alternative aspect of the invention, the substrate has an irregular surface to enhance deformations of portions of the conductive path in response to motions of a subject mechanically interfaced with the transducer element.

In yet another aspect of the invention, an apnea detection system is provided for detecting the cessation of breathing movement in an infant or other being. This system includes a continuous electrically conductive serpentine path formed of resilient material. The path has a width which is relatively narrow with respect to its length and has an electrical resistance which varies in response to deformations of the resilient material forming the path. Means are also provided for electrically insulating the sides of the serpentine path from each other in order to avoid short circuiting between adjacent side portions of the path. A control means is connected to the resilient material for detecting variations in the impedance of the conductive path. The control means is operative to generate an alarm signal whenever variations in the resistance of the path fall below a predetermined level.

Still other objects of the present invention will become readily apparent to those skilled in this art from the following description wherein there is shown and described a preferred embodiment of this invention, simply by way of illustration of one of the best modes contemplated for carrying out the invention. As will be realized, the invention is capable of other different embodiments, and its several details are capable of modification in various, obvious aspects, all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description serve to explain the principles of the invention. In the drawings.

Reference will now be made in detail to the present preferred embodiment of the invention, an example of which is illustrated in the accompanying drawings.

DETAILED DESCRIPTION OF THE PREFERRED EMBODIMENT

As used in the present specification and claims, the term "mechanical interface" will be used to describe a physical relationship wherein one subject is positioned relative to another subject such that the physical movement of said one subject mechanically transmits a pressure to the other subject. The term "subject" will be used to describe either a human or other animal or an inanimate object. The term "resilient" will be used to describe a property of a material that enables it to essentially resume its original shape after deformation sufficient to materially alter the material's dimensions.

Figure 1:
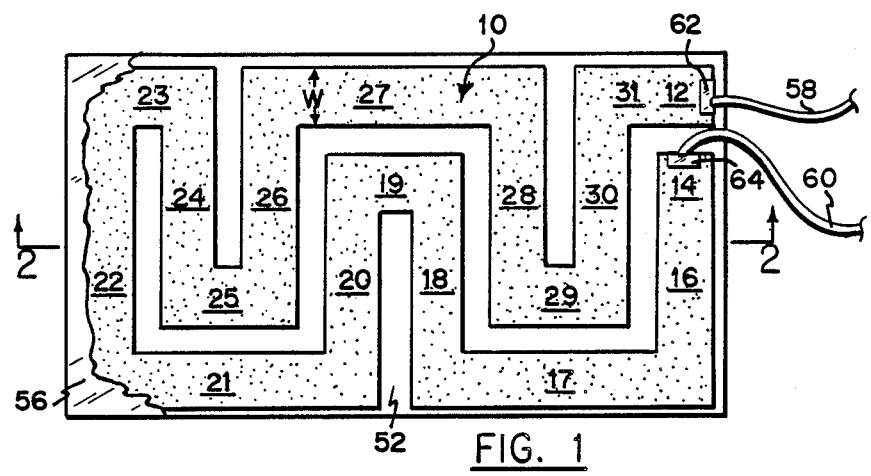
FIG. 1 is a plan view of a transducer element constructed in accordance with the principles of the present invention with the protective enclosure partially removed to depict a continuous serpentine path of resilient material.

Referring now to the drawings, FIG. 1 shows a transducer element 10 constructed in accordance with the principles of the present invention for detecting movements of a mechanically interfaced subject. The transducer element of the invention is resiliently deformable and is designed to detect the movements of the mechanically interfaced subject by variations in localized deformations of the transducer element caused by such a subject. By way of specific example, the illustrated transducer element 10 will be described as being used for detecting breathing movements of an infant. A control circuit used in conjunction with the transducer element 10 will be disclosed hereinafter for generating an alarm signal whenever the detected movements of the infant mechanically interfaced with the transducer element cease for a predetermined period of time.

The illustrated transducer element 10 of FIG. 1 is formed of a single piece of electrically resistive material extending from a first transducer element end 12 to a second transducer element end 14, said electrically resistive material forming a continuous conductive path between the ends 12,14. This continuous conductive path defined by the transducer element 10 has a width, W, which is relatively narrow with respect to its length, the length being the winding distance extending between the first and second ends 12,14. In the illustrated embodiment of FIG. 1, for example, the length of the conductive path is many multiples of the width, W.

As also shown in FIG. 1, the conductive path formed through the transducer element 10 is arranged in a nonoverlapping serpentine configuration to permit the relatively narrow conductive path to substantially cover a predetermined detection area. The serpentine configuration includes a series of legs 16-31 joined by turns in the conductive path. Each of the serpentine legs is substantially coplanar with the remaining legs, as most clearly illustrated in FIG. 2, and arranged to form a padlike structure.

In the preferred form of the invention, the transducer 10 is formed of a resilient plastic foam material impregnated with a conductive substance, such as graphite. Preferably, the transducer element has an electrical conductivity in the semiconductor range. One presently available conductive foam material is commercially sold under the trademark VELOSTAT by Minnesota Mining and Manufacturing Company of Minneapolis, Minn.

Turning once again to FIG. 2, the transducer element 10 is shown supported upon a substrate 52. The substrate 52 is formed of nonconductive material so as to avoid short circuiting the conductive path between the various legs 16-31 of the transducer element 10. Preferably, the transducer element 10 is adhesively or otherwise secured to the substrate 52. In this way, the substrate 52 functions to maintain the integrity of the spacial relationships between the serpentine legs 16-31 shown in FIG. 1. Specifically, the substrate 52 of the illustrated embodiment maintains an interposed insulating air gap between the various legs of the serpentine arrangement as, for example, between serpentine legs 16 and 30 and between legs 17 and 29. It should be noted, however, that the substrate 52 is not necessary for operation of the transducer element 10, and the insulating function served by the substrate 52 may be achieved with various other methods known to those skilled in the art.

Figure 2:
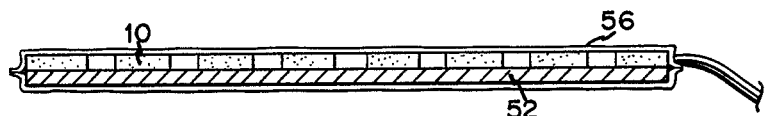
FIG. 2 is a cross-sectional view of the transducer element of FIG. 1 taken across line 2—2 in FIG. 1 showing the serpentine conductive path supported upon a substrate with both the path and the substrate being disposed within a protective enclosure.

As shown in both FIGS. 1 and 2, a flexible protective cover 56 is provided in the preferred embodiment for enclosing both the transducer element 10 and the substrate 52. The protective cover 56 is electrically insulating and preferably waterproof. In the preferred embodiment, the protective cover 56 is formed of a flexible plastic material. It should be noted that the nonconductive, protective cover 56 may serve as both a cover and a substrate for the transducer element. It may also be desirable to electrically shield the conductive path 10 from electrical background noise. One way this may be achieved would be to form the insulating protective cover 56 from a multi-ply structure having an intermost electrically insulating ply and at least one other conductive ply. The conductive ply in such an arrangement would function to shield the conductive path from electrical noise. As those skilled in the art will readily appreciate, the conductive ply should be grounded.

FIG. 1 further depicts a pair of conductors, specifically illustrated as wires 58 and 60, connected to the first and second transducer element ends 12 and 14 respectively. Wire 58 is secured to the first transducer element end 12 by a wire attachment device, shown as a metal clamp 62, while wire 60 is similarly secured to the second transducer element end 14 by a metal clamp 64.

The padlike structure formed by the resilient transducer element 10 may be placed on the mattress of a baby crib or bassinet to provide a subjacent sleeping support surface for an infant. When an infant is mechanically interfaced to the transducer element 10 by being placed thereon, the infant's repeated breathing movements will exert a varying pressure upon localized areas of the transducer element 10, and this varying pressure will cause the transducer element 10 to be varyingly deformed in a direction normal to the conductive path at these localized areas. As indicated above, the transducer element 10 is resilient and will essentially return to its original shape once the pressure causing the deformation is removed. Continual breathing movements of an infant will thus result in a correspondingly continual variation in the cross-sectional dimensions of one or more of the transducer element legs 16-31 by virtue of the repeated deformation and recoil of localized areas on the legs of the transducer element 10. Such variations in the cross-sectional transducer element leg dimensions result in corresponding variations in the electrical impedance of the conductive path through the transducer element 10. So long as a mechanically interfaced infant continues to breath, the resulting movements will vary the impedance of the conductive path. As will be explained in greater detail below, this continual variation in the transducer element impedance is used as an indication that the infant is breathing.

As will be apparent to those skilled in the art from the foregoing description, the relatively narrow width of the transducer element 10 operates to maximize the change in the overall impedance of the transducer element 10 from deformation of a relatively small portion of that transducer element. In other words, the relative narrowness of the legs of the transducer element 10 maximize the percentage of the cross section of the conductive path which is deformed relative to the percentage of that same cross section conductive path which remains undeformed. In short, since current flows serially through each and every cross-sectional area of the conductive path, the more narrow the path width, the more a relatively small deformation will vary the overall transducer element impedance. The relatively narrow transducer element 10 is thus highly responsive to even relatively small deformations anywhere within the conductive path. However, if the conductive path through the transducer element 10 becomes too narrow, the overall impedance of the transducer element will become so great that satisfactory signal conditioning of the current flowing through the transducer element 10 becomes problematic. Therefore, as a tradeoff, the path width, W, is preferably selected along with the path length, L (not shown in the drawing), so that the overall transducer element resistance is less than several megohms. In one of the preferred embodiments designed for use in a conventional baby crib, a quarter inch thick graphite impregnated strip of approximately 2½ inches in width and 32 feet in length is arranged in a serpentine fashion to cover a detection area of approximately 2 feet by 4 feet.

It will also be appreciated that the serpentine arrangement of the transducer element 10 allows the relatively narrow strip of transducer element material to substantially cover the entire detection area defined by the padlike structure. Since the infant may well move anyplace within the baby crib or bassinet during sleep, it is highly desirable to have the detection area correspond to the entire sleeping surface supporting the infant.

Figure 3:
FIG. 3 is a modified form of the substrate of FIG. 2 having an irregular surface for enhancing deformations of the foam conductive path caused by a mechanically interfaced subject.

The parameters to optimize when constructing the transducer element include the median length, L, of the continuous path of sensor material, along with its cross-sectional area, A. These two parameters determine the overall resistance, R, of the transducer element pad for any given resistive material having a coefficient of resistivity, p. That is, $R = p(L/A)$. A broad range of $(L/A)$ values has been found suitable for commonly available, graphite-impregnated foam. Unfortunately, transducer element pad resistance is quite high for a normal size sleeping area. Resistance is high because the pad sensor material is configured in a series manner, as opposed to a parallel construction which would result in a decrease in transducer element resistance. The major problem of such a large resistance transducer element pad is the relative ease of coupling of electrical noise from the environment into the signal conditioning electronics. Fortunately, the signal conditioning circuitry can be made to handle both the high transducer element resistance and the additional noise input. One means of reducing the magnetic component of electromagnetic noise is to configure the path of the serpentine turns in such manner that the loop area of the transducer element is minimized as shown in FIG. 1. In the illustrated embodiment, the ends 12 and 14 are juxtaposed, an arrangement which further assists in reducing the loop area enclosed by the conductive path. It is anticipated that the electrical component of said noise could also be compensated for by configuring the strip of sensor material into two or four symmetrical pads. By this means, the symmetrical pads could be made part of a transducer element bridge circuit, thereby allowing subtraction of some or all of the background electrical noise. Where environmental electrical noise is excessive, a flexible, conductive shield may be utilized to insure immunity from such noise sources. Another means for increasing the signal to noise ratio is the utilization of a non-conductive substrate having an irregular surface to enhance deformations caused by the breathing motions. One possible irregular surface is the so-called "egg crate" foam 50 depicted in FIG. 3 to enhance the pad deformation caused by breathing motions. This "egg crate" material 50 may be substituted for the substrate 52 of FIG. 2.

Figure 4:
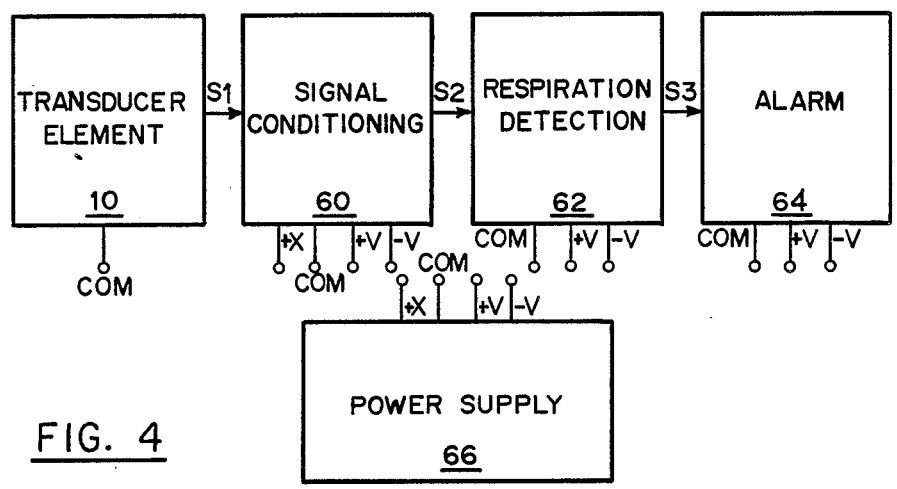
FIG. 4 is a schematic depiction showing the functional elements of a control circuit for use with the transducer element of FIGS. 1 and 2 for detecting the cessation of movement of a mechanically interfaced subject.

FIG. 4 is a simplified schematic block diagram of one measurement scheme which may be used for activating an alarm in response to breathing cessation of an infant mechanically interfaced with the illustrated transducer element 10. As depicted in the FIG. 4 diagram, the transducer element output signal S1 is applied to signal conditioning circuitry represented by block 60. The conditioned signal S2 output from the signal conditioning circuitry of block 60 is applied to detection circuitry, represented by block 62. The detection circuitry compares the conditioned signal S2 against both high and low predetermined threshold values and produces an output signal S3 indicative of whether or not the signal S2 has exceeded these threshold levels. In the described embodiment, the conditioned signal S2 will fail to reach either of these threshold values whenever the variations of signal S1 fall below a predetermined level, a condition indicative of cessation of breathing by the infant mechanically interfaced with the transducer element 10.

The signal S3 is applied to a timer of an alarm circuit represented by block 64. If the signal S3 indicates that signal S2 has not exceeded the threshold values for a predetermined period (determined by a timer), an alarm is activated to indicate a detected apnea condition. As indicated by block 66 in FIG. 4, each of the circuits 60, 62 and 64 are supplied by a common power supply 66.

Figure 5:
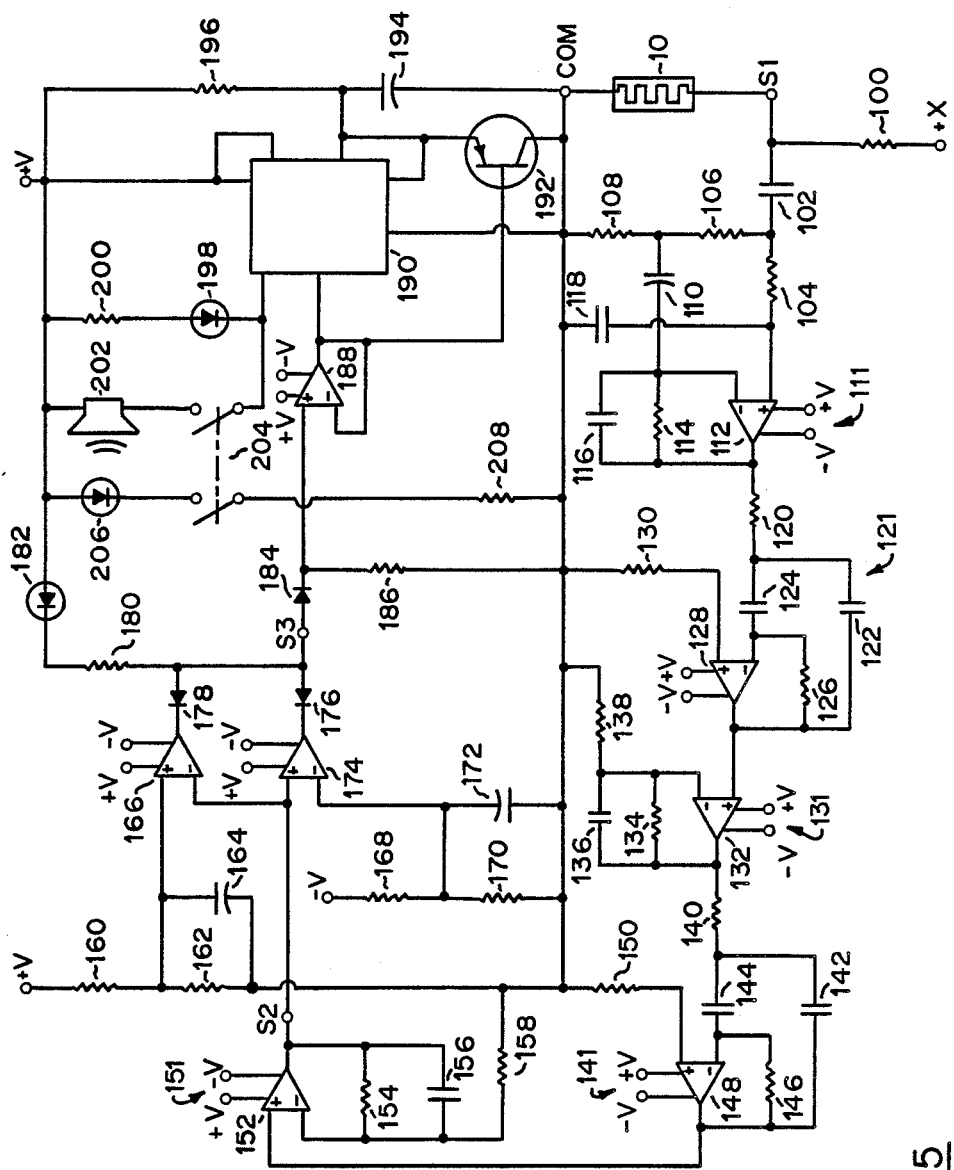
FIG. 5 depicts one electrical circuit for implementing the control scheme of FIG. 4.

One circuit for implementing the control scheme of FIG. 4 is shown in FIG. 5. As shown, a bias resistor 100 applies a bias voltage from the +X output of the power supply 66 to transducer element 10 at the junction of resistor 100 and transducer element 10. As previously described, a varying electrical signal results when the impedance of the transducer element 10 changes. Signal S1 from transducer element 10 is thus composed of the bias voltage, a varying electrical signal resulting from deformations of the transducer element 10 and electrical background noise signals. Coupling capacitor 102, together with input bias resistor 106 of operational amplifier 112 function to transfer only varying electrical signal components from signal S1 into the amplification and filtering circuit of block 60 in FIG. 4. The varying electrical signal from the transducer element 10 is boosted by a noninverting amplifier 111 formed by operational amplifier 112, capacitor 110 and resistors 108 and 114. High input impedance of this amplifier 111 is achieved by utilizing feedback from the output of operational amplifier 112 through capacitor 110 to cause the same AC voltage to appear at both ends of the bias resistor 106 Resistor 104 and capacitor 118 filter out some high frequency noise signals. Feedback capacitor 116 removes additional high frequency noise from the amplified signal output of operational amplifier 112.

Elements 120,122,124,126,128 and 130 form a bandpass filter 121 for extracting the desired signal from unwanted low and high frequency components of the signal that is output from operational amplifier 112. To further boost the signal level, the output of the bandpass filter 121 is amplified by a further noninverting amplifier 131 formed from elements 132,134,136 and 138. The output of this further noninverting amplifier 131 feeds a second bandpass filter 141 comprised of elements 140,142,144,146,148 and 150. The output of this second bandpass filter 141 is then applied to another noninverting amplifier 151 made up of elements 152,154,156 and 158, and results in signal S2 being output from operational amplifier 152.

Continuing to refer to FIG. 5, signal S2 is applied to the detection circuit 62 of FIG. 4. Resistors 160 and 162 cooperate with capacitor 164 and an amplifier 166 to form a positive voltage level threshold comparator for comparing variations in the conditioned signal S2 against a predetermined positive voltage level. Similarly, resistors 168 and 170 cooperate with capacitor 172 and amplifier 174 to form a negative voltage level threshold comparator to compare the same voltage signal S2 against a predetermined negative voltage level. Diodes 176 and 178 connect the outputs of the two comparators together so as to produce signal S3. The output of each comparator remains at a high level until signal S2, which is input to each comparator, varies beyond that comparator's threshold level. Clearly then, signal S3 remains at a high level until the magnitude of signal S2 changes sufficiently in the positive or negative direction to exceed either comparator's threshold, at which time signal S3 switches low. Signal S3 remains low until the magnitude of signal S2 falls below the threshold of the switched comparator. Whenever signal S3 is switched low, current flows through current limiting resistor 180 and LED 182 thereby indicating that respiration or movement has been detected.

Signal S3 of FIG. 5 is input into the alarm circuit 64 of FIG. 4. Diode 184, resistor 186 and buffer amplifier 188 function to apply only the positive transitions of signal S3 to the timer device 190 and a transistor 192. In the configuration shown, a high to low transition of signal S3 triggers, as well as resets, timer device 190. Capacitor 194 and resistor 196 determine the duration interval for timing of the timing device 190. As long as respiration continues to be detected, that is as long as signal S3 does not remain at a high level longer than the duration interval for timing, the output of timer device 190 will remain at a high level. Under these conditions, no alarm is activated. On the other hand, if signal S3 does not change to its low state before the duration interval for timing has elapsed, then the output of timing device 190 switches from a high to a low level. Whenever the output of timing device 190 is low, current flows through the resistor 200 and LED 198 to indicate an alarm condition. An alarm condition will cause acoustic alarm 202 to sound if switch 204 is closed. Also, the acoustic alarm may be inactivated by opening switch 204. LED 206 indicates that the acoustic alarm is enabled whenever the switch 204 is closed, because current is then allowed to flow through LED 206 and current limiting resistor 208.

In summary, numerous benefits have been described which result from employing the concepts of the invention. The described transducer element may be placed on a sleeping support surface, such as a mattress, to detect even subdued breathing movements of an infant. Significantly, the transducer element is not attached to the infant, and it does not limit the infant's movement or cause discomfort. Further, the serpentine arrangement of the transducer element may be expanded to cover a detection area adequate to cover the entire sleeping support surface of a infant's crib while maintaining transducer element sensitivity. The serpentine configuration of the transducer element may also be arranged wherein opposite longitudinal ends are juxtapositioned to reduce the loop area of the transducer element and to thereby minimize electrical background noise. The low cost and convenience of the described transducer element also makes monitoring of even low risk infants practical.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, the transducer element could be configured as a jacket mechanically interfaced about an infant. Also, various different measurement techniques and alternate circuit configuration may be used with the invention. It is also contemplated that the invention could be used to monitor heartbeats or to detect seizures. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

I claim:

1. A transducer element for monitoring movement of a subject mechanically interfaced therewith, comprising:

(a) a continuous electrically conductive path formed of resilient electrically resistive material, said conductive path having a width which is relatively narrow with respect to its length, said electrically resistive material being resiliently deformable in a direction perpendicular to the conductive path and having an electrical impedance which varies in response to variable resilient deformations of localized areas of said resilient material when said deformations have a directional component perpendicular to the conductive path, said conductive path being configured into a serpentine shape to form a series circuit of conductive path legs joined by turns, said serpentine conductive path covering a predetermined detection area;

(b) a substrate for electrically insulating the legs of the serpentine conductive path from each other except through the conductive path turns, said conductive path being secured to said substrate to maintain a spacing between adjacent legs of the serpentine conductive path, said substrate having a non-uniform surface of peaks and valleys to enhance deformations of localized areas of the electrically resistive material in a direction perpendicular to the conductive path in response to motions of a subject supported on the transducer element; and (c) an electrical conductor connected to each end of the continuous path, said conductors being electrically connected with each other through the conductive path.

* * * * *